(12) United States Patent
Morgan et al.

(10) Patent No.: US 9,827,342 B2
(45) Date of Patent: Nov. 28, 2017

(54) PERFUME MIXTURES COMPRISING AN OLFACTIVE INDEX FOR ACTIVATED AIR FRESHENERS

(71) Applicant: The Procter & Gamble Company, Cincinnati, OH (US)

(72) Inventors: George Kavin Morgan, Hamilton, OH (US); Zaiyou Liu, West Chester, OH (US); David Thomas Stanton, Hamilton, OH (US); Ronald David Turner, Walton, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/744,350

(22) Filed: Jun. 19, 2015

(65) Prior Publication Data

US 2016/0367713 A1    Dec. 22, 2016

(51) Int. Cl.
*A61L 9/01* (2006.01)
*C11B 9/00* (2006.01)

(52) U.S. Cl.
CPC . *A61L 9/01* (2013.01); *C11B 9/00* (2013.01)

(58) Field of Classification Search
CPC ..................................... C11B 9/00; A61L 9/01
See application file for complete search history.

(56) References Cited

U.S. PATENT DOCUMENTS

| | | | |
|---|---|---|---|
| 6,729,552 B1 | 5/2004 | McEwen et al. | |
| 6,793,149 B2 | 9/2004 | Schramm et al. | |
| 7,441,755 B2 * | 10/2008 | O'Leary | A01M 1/2044 239/44 |
| 7,648,127 B2 | 1/2010 | Cittadino | |
| 7,909,264 B2 | 3/2011 | Dunne et al. | |
| 2007/0257016 A1 | 11/2007 | Jin et al. | |
| 2010/0028289 A1* | 2/2010 | Diersing | A61K 8/31 424/76.2 |

FOREIGN PATENT DOCUMENTS

| | | |
|---|---|---|
| CA | 2007854 A1 | 3/1991 |
| EP | 253640 A2 | 1/1988 |
| EP | 0 672 425 A1 | 9/1995 |
| EP | 1849485 A1 | 10/2007 |
| WO | WO 97/25662 A1 | 7/1997 |
| WO | WO98/58684 A1 | 12/1998 |
| WO | WO03/086488 A1 | 10/2003 |
| WO | WO2005/000018 A1 | 1/2005 |
| WO | WO 2008/100411 A1 | 8/2008 |
| WO | WO2011/106889 A1 | 9/2011 |
| WO | WO2012/107527 A1 | 8/2012 |
| WO | WO 2014/195689 A1 | 12/2014 |
| WO | WO 2014/201339 A1 | 12/2014 |

OTHER PUBLICATIONS

U.S. Appl. No. 14/744,360, filed Jun. 19, 2015, Ronald David Turner, et al.
PCT Search Report PCT/US2016/036312; dated Aug. 17, 2016; 11 Pages.
PCT Search Report PCT/US2016/036309; dated Jul. 26, 2016; 16 Pages.
All Office Actions P&G U.S. Appl. No. 14/744,360.

* cited by examiner

*Primary Examiner* — Lanee Reuther
(74) *Attorney, Agent, or Firm* — Abbey A. Lopez

(57) ABSTRACT

A perfume mixture comprising an olfactive index and vapor pressure distribution for improved diffusion from activated air fresheners and methods thereof are provided.

12 Claims, 1 Drawing Sheet

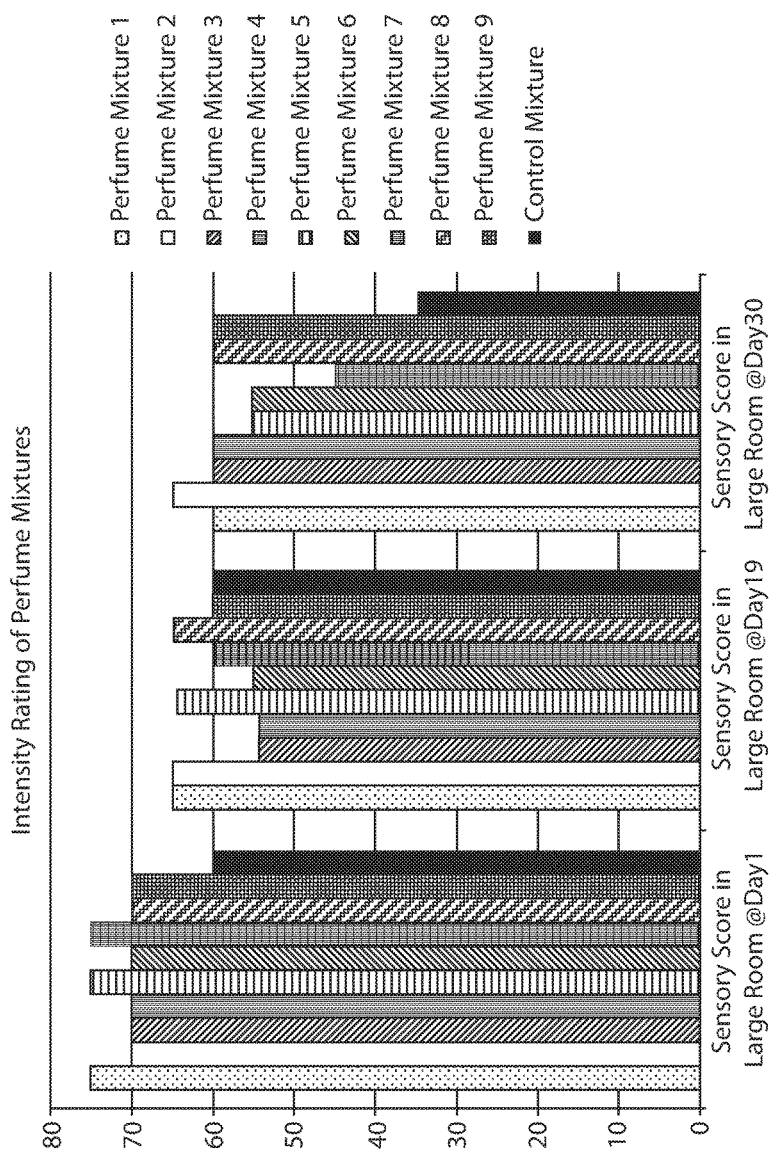

PERFUME MIXTURES COMPRISING AN OLFACTIVE INDEX FOR ACTIVATED AIR FRESHENERS

FIELD

The present invention relates to perfume mixtures comprising an olfactive index and vapor pressure distribution for improved diffusion from activated air fresheners and methods thereof.

BACKGROUND

Various devices in the marketplace provide emission of a volatile perfume mixture over a period of time using a diffusion assistance means, such as heating elements, piezoelectric elements, and motorized fans. While energized assistance of such devices facilitates diffusing the perfume mixture, often times, this leads to quicker perfume mixture end-of-life and/or a less consumer desirable scent experience with high initial scent intensity. Approaches to lengthen the duration of emission of the perfume mixture include formulating less volatile (i.e. lower vapor pressure) perfume materials in the perfume mixture and using a larger volume of the perfume mixture in the device. However, these approaches may not achieve a consumer acceptable scent experience and may involve higher costs for the increased amount of perfume mixture and/or the increased amount of perfume raw materials that are formulated into the perfume mixture.

There remains a need for perfume mixtures providing consumer desirable scent experiences and longevity, while minimizing the amount of perfume mixture and perfume raw materials necessary to achieve such experience and longevity.

SUMMARY

According to one embodiment, there is provided a perfume mixture comprising an olfactive index of at least about 12,000, wherein said perfume mixture comprises at least about 5 wt. % of perfume raw materials having an odor detection threshold less than or equal to about 1 ppb, and comprises about 45 wt. % to about 85 wt. % of perfume raw materials having a weighted average vapor pressure range from about 15,000 ppb to about 20,000 ppb.

According to another embodiment, there is provided a method of formulating a perfume mixture for use with an energized air freshener comprising the steps of calculating the average olfactive index of said perfume mixture, and selecting perfume raw materials that provide a perfume mixture with an average olfactive index of at least about 12,000.

According to yet another embodiment, there is provided a perfume mixture comprising an olfactive index of at least about 12,000, wherein said perfume mixture comprises at least about 5 wt. % of perfume raw materials having an odor detection threshold less than or equal to about 1 ppb, and a sensory intensity rating of greater than or equal to 45.

BRIEF DESCRIPTION OF DRAWINGS

The above-mentioned and other features and advantages of the present disclosure, and the manner of attaining them, will become more apparent and the present disclosure itself will be better understood by reference to the following description of various embodiments of the present disclosure taken in conjunction with the accompanying drawings, wherein:

FIG. 1 is graph showing the scent intensity of various perfumes mixtures.

DETAILED DESCRIPTION

"Energized" as used herein refers to an apparatus or system that operates by using an electrical energy source, such as a battery or electrical wall outlet, to diffuse or emit a targeted active such as a perfume mixture.

It should also be understood that when the perfume mixture is described herein as being "delivered" or "emitted" or "diffused", this refers to the volatilization of the volatile component therein, and does not require that the non-volatile components therein be emitted.

The features illustrated or described in connection with one example embodiment can be combined with the features of other example embodiments. Such modifications and variations are intended to be included within the scope of the present disclosure.

For example, the perfume mixture may be contained in a reservoir having a fluid transport member for use with an energized device. An exemplary energized device may be an electrical heating device. More particularly, the device may be an electrical wall plug air freshener having a wick as described in U.S. Pat. No. 7,223,361; a battery powered heating device; or other heating devices (e.g. devices powered by chemical reactions such as catalyst fuel systems; solar powered devices, etc.). In such devices, the wick may be placed next to the heating surface to diffuse the volatile material. The perfume mixture may also be contained in a reservoir for use with an air purifying system or a fan-based air freshener to deliver volatile materials to the atmosphere.

The perfume mixture of the present invention delivers a volatile material in a substantially continuous manner when the device is activated. The emission level of volatile materials may exhibit a uniform intensity until substantially all the volatile materials are exhausted. The continuous emission of the volatile materials can be of any suitable length, including up to: 20 days, 30 days, 60 days, or longer periods.

Perfume Mixture

The perfume mixture of the present invention may comprise at least one perfume raw material ("PRM"). Most conventional PRMs are volatile essential oils. The PRM can be a volatile organic compound commonly available from perfumery suppliers. Furthermore, the PRM can be synthetically or naturally formed materials. Examples include oil of bergamot, bitter orange, lemon, mandarin, caraway, cedar leaf, clove leaf, cedar wood, geranium, lavender, orange, origanum, petitgrain, white cedar, patchouli, neroili, rose absolute, and the like.

While not wishing to be bound by theory, the continuous delivery of a PRM may be a function of various factors. These factors include the physical properties of a PRM such as molecular weight and saturation vapor pressure ("VP"), odor detection threshold ("ODT"), etc.; the type of fluid transport member (e.g. pore size, surface area, etc.) used to diffuse the PRM; environmental factors such as heat, air flow, etc.; the existence of the viscosity and/or surface tension of the perfume mixture containing the PRM; etc.

It has surprisingly been found that the combination of certain VPs and ODTs have an olfactive index ("OI") that not only provides consumer desirable scent intensity and longevity, but also consumer desirable scent character. The perfume mixture of the present invention may have an OI of greater than about 12,000, or greater than about 20,000, or greater than about 25,000, or greater than about 28,000, or from about 12,000 to about 500,000, or from about 20,000 to about 100,000, or from about 25,000 to about 100,000, or from about 25,000 to about 80,000, or from about 25,000 to about 60,000, or from about 40,000 to about 60,000.

OI is calculated by the following equation:

$$OI = \sum_i \frac{x_i \cdot P_{vap,i}^{sat,25C}}{ODT_i}$$

where OI is defined as an olfactive index of a given perfume composition; $P_{vap,i}^{sat,25C}$ is the VP of a volatile PRM$_i$ at 25° C. expressed in units of ppb; $x_i$ is the molar percent of PRM$_i$ in the perfume composition; and ODT$_i$ is the odor detection threshold of PRM$_i$ expressed in units of ppb; and where all PRMs in the perfume composition are included in the calculated OI value.

VP of individual PRMs can be calculated using the Advanced Chemistry Development Labs ("ACD") (Toronto, Canada) VP computational model, version 14.02 providing VP values at 25° C. expressed in units of torr, and then converted to partial pressure expressed as ppb, based directly on the molecular structure.

ODT of individual PRMs can be calculated using the test method outlined herein, based directly on the molecular structure of the given PRM, and expressed in units of ppb. The OI calculation can be used in selecting PRMs for perfume mixtures for use, for example, in energized air fresheners.

Generation of Molecular Descriptors

For each PRM in a perfume mixture or composition, its molecular structure is used to compute various molecular descriptors. The molecular structure is determined by the graphic molecular structure representations provided by the Chemical Abstract Service ("CAS"), a division of the American Chemical Society, Columbus, Ohio, U.S.A. These molecular structures may be obtained from the CAS Chemical Registry System database by looking up the index name or CAS number of each PRM. For PRMs, which at the time of their testing are not yet listed in the CAS Chemical Registry System database, other databases or information sources may be used to determine their structures. For a PRM which has potentially more than one isomer present, the molecular descriptor computations are conducted using the molecular structure of only one of the isomers, which is selected to represent that PRM. The selection of isomer is determined by the relative amount of extension in the molecular structures of the isomers. Of all the isomers of a given PRM, it is the isomer whose molecular structure has the most extended configuration which is the one that is selected to represent that PRM. The structures for other potential isomers of that PRM are excluded from the computations. The molecular structure of the isomer with the most-extended configuration is paired with the molar % concentration of that PRM, where the molar % reflects the presence of all the isomers of that PRM that are present.

A molecule editor or molecular sketching software program, such as ChemDraw (CambridgeSoft/PerkinElmer Inc., Waltham, Mass., U.S.A.), is used to duplicate the 2-dimensional molecular structure representing each PRM. Molecular structures should be represented as neutral species (quaternary nitrogen atoms are allowed) with no disconnected fragments (e.g., single structures with no counter ions). The winMolconn program described below can convert any deprotonated functional groups to the neutral form by adding the appropriate number of hydrogen atoms and will discard the counter ion.

For each PRM, the molecular sketching software is used to generate a file which describes the molecular structure of the PRM. The file(s) describing the molecular structures of the PRMs is subsequently submitted to the computer software program winMolconn, version 1.0.1.3 (Hall Associates Consulting, Quincy, Mass., U.S.A., www.molconn.com), in order to derive various molecular descriptors for each PRM. As such, it is the winMolconn software program which dictates the structure notations and file formats that are acceptable options. These options include either a MACCS SDF formatted file (i.e., a Structure-Data File); or a Simplified Molecular Input Line Entry Specification (i.e., a SMILES string structure line notation) which is commonly used within a simple text file, often with a ".smi" or ".txt" file name extension. The SDF file represents each molecular structure in the format of a multi-line record, while the syntax for a SMILES structure is a single line of text with no white space. A structure name or identifier can be added to the SMILES string by including it on the same line following the SMILES string and separated by a space, e.g.:

C1=CC=CC=C1 benzene.

The winMolconn software program is used to generate numerous molecular descriptors for each PRM, which are then output in a table format. Specific molecular descriptors derived by winMolconn are subsequently used as inputs (i.e., as variable terms in mathematical equations) for the ODT model test method in order to calculate the ODT value for each PRM. The molecular descriptor labels used in the ODT model test method computations are the same labels reported by the winMolconn program, and their descriptions and definitions can be found listed in the winMolconn documentation. The following is a generic description of how to execute the winMolconn software program and generate the required molecular structure descriptors for each PRM in a composition.

Computing Molecular Structure Descriptors Using winMolconn:

1) Assemble the molecular structure for one or more perfume ingredients in the form of a MACCS Structure-Data File, also called an SDF file, or as a SMILES file.

2) Using version 1.0.1.3 of the winMolconn program, running on an appropriate computer, compute the full complement of molecular descriptors that are available from the program, using the SDF or SMILES file described above as input.
   a. The output of winMolconn is in the form of an ASCII text file, typically space delimited, containing the structure identifiers in the first column and respective molecular descriptors in the remaining columns for each structure in the input file.

3) Parse the text file into columns using a spreadsheet software program or some other appropriate technique. The molecular descriptor labels are found on the first row of the resulting table.

4) Find and extract the descriptor columns, identified by the molecular descriptor label, corresponding to the inputs required for each model.
   a. Note that the winMolconn molecular descriptor labels are case-sensitive.

Test Method for Determining ODT

The ODT value is computed for each free PRM identified in the perfume mixture through the use of the computational ODT model provided herein written in the Java programming computer language. The program source code for the ODT model is provided herein as two parts, for ODTNeuralNetworks.java and ODTNeuralNetworksDescriptors.java, in word processor text format. Both Java classes are needed to execute the model. The ODTNeuralNetworksDescriptors class is a data container whose purpose is to ensure that molecular descriptors required to execute the neural network are provided to the network in the proper order. The ODTNeuralNetworks class contains the neural network equations, and expects an instance of the ODTNeuralNetworksDescriptors class as input. These two Java source code class files must be combined with other code written by the user, which will add the winMolconn descriptor data required to the ODTNeuralNetworksDescriptors instance, and then pass that object to an instance of ODTNeuralNetworks, and then retrieve the result. These classes expect to be run under the Java software platform version 1.7 or higher (Sun Microsystems/Oracle Corporation, Redwood Shores, Calif., U.S.A.).

Attached herewith is a compact disc having the above-referenced program source code saved as "ODTNeuralNetworks" and "ODTNeuralNetworksDescriptors" ("CD-R"). The word processor text format files were created on Apr. 21, 2015 and contain 141 bytes and 17 bytes of data, respectively. The CD-R is hereby incorporated by reference in its entirety.

The model used to compute ODT values is based on the ODT data provided in the book "Standardized Human Olfactory Thresholds" (Devos, M.; Patte, F.; Rouault, J.; Laffort, P.; Van Gernert, L. J.; Standardized Human Olfactory Thresholds; IRL: Oxford, England, 1990.). In this context, human ODTs are expressed as olfactory power (p.ol) (the negative of the base 10 log of the molar concentration of the odorant in air at which a human first detects the presence of the odorant). These values can be directly transposed to other commonly used units such as ppm (volume) and ppb (volume): thresholds of 1 ppm and 1 ppb are equivalent to p.ol=6 and p.ol=9, respectively. The ODT computational model itself is a set of ten individual computational neural-net ("CNN") models written in the Java programming language. The outputs of all ten CNN models are averaged, and the average p.ol value is reported along with the standard deviation of the set of predicted values.

The starting information required to conduct the ODT computed-value test method which follows, includes the identity and molecular structure of each PRM in the perfume mixture being tested, and the values of various computationally-derived molecular descriptors for each of those PRMs, as determined in accordance with the respective test methods described herein. Additionally, the weight percent of each PRM is also required in order calculate the OI of a perfume mixture.

The specific winMolconn-derived molecular descriptors required for the ODT computation include:
nasS=Count of sulfur atoms;
Hmax=Highest Atom Level HE-State (Site of the most polar hydrogen atom);
fw=Formula weight of the structure;
xc3=$3^{rd}$-order cluster molecular connectivity index;
numHBa=Count of hydrogen-bond accepting atoms;
e2C3O1s=Sum of bond-type electrotopological state indexes for double bonds between an oxygen atom and a carbon atom attached to two other non-hydrogen atoms;
e1C3O1d=Sum of bond-type electrotopological state indexes for single bonds between an hydroxyl oxygen atom and an $sp^2$ carbon atom attached to two other non-hydrogen atoms;
SssCH2=Sum of the electrotopological state index values for methylene ($-CH_2-$) carbon atoms;
xv1=Valence-corrected $1^{st}$-order molecular connectivity index;
SHHBa=Sum of electrotopological state index values for all hydrogen bond accepting atoms in the molecule;
nasO=Count of oxygen atoms;
e2C2O1=Sum of the electrotopological state indexes for double bonds between an oxygen atom and a carbon atom attached to one hydrogen atom and one non-hydrogen atom;
nasC=Count of carbon atoms;
SHHBd=Sum of the hydrogen atom electrotopological state indexes for all hydrogen atoms on hydrogen-bond donating atoms;
nrbond=Count of rotatable bonds;
nelem=Count of element types;
SsCH3=Sum of the electrotopological state indexes for the methyl-group ($-CH_3$) carbon atoms;
eaC2C2a=Sum of bond-type electrotopological state indexes for aromatic bonds between two unsubstituted aromatic carbon atoms;
e1C3O1a=Sum of bond-type electrotopological state indexes for single bonds between a hydroxyl oxygen atom and an aromatic ring carbon atom;
SHCsatu=Sum of the hydrogen atom electrotopological state indexes for hydrogen atoms on $sp^a$ carbons that are also bonded to $sp^2$ carbon atoms;
Qv=Electrotopological state polarity index;
nvx=Count of graph vertices (a count of non-hydrogen atoms).

The specific molecular descriptors are output by the winMolconn software in a table format. The ODT model itself is provided in the ODTNeuralNetworks class. The ODTNeuralNetworksDescriptors helper class provides the setter methods that allow the individual descriptors to be added to the instance of the helper in any order. The getOrderedDescriptors( ) method of the helper class returns the ordered descriptor array required for the neural network model. To execute the ODT model, it is necessary to create a main class that will: 1) create an instance of the of the helper class, 2) populate the instance of the helper class with the required descriptor values from winMolconn, 3) pass ordered descriptor array from the helper class to an instance of the ODT model, 4) and then get the computed ODT value back from the model instance using the getODTModelResult( ) method. The main class is expected to be provided by the user, and is responsible for reading in the winMolconn descriptors, and for reporting the computed ODT value derived from the model for each PRM.

The ODT model is in the form of a CNN. Each CNN is implemented in Java (version 1.7) with each network being embodied in a single Java class object. In order to execute the ODT model, it is necessary to wrap the model class with a Java main class that will create the necessary inputs for the model class, instantiate and execute the class, and then retrieve and report the result. The CNN model class has an associated Descriptor class that is needed to provide the model inputs to the CNN in the proper order. The Java main class should instantiate the respective descriptor class, add the required winMolconn descriptors to the descriptor class instance, and then pass that instance of the descriptor class to the CNN instance as an argument.

Computing the Odor Detection Threshold:
1) Create a Java main executable class that will create and access instances of the ODTNeuralNetworksDescriptors and ODTNeuralNetworks classes provided herein.
2) For each perfume raw material of interest:
   a. Using the winMolconn program (version 1.0.1.3), compute the full complement of available molecular descriptors.
   b. From the output of winMolconn, extract values of the following molecular descriptors: nasS, Hmax, fw, xc3, numHBa, e2C3O1s, e1C3O1d, SssCH2, xv1, SHBa, nasO, e2C2O1, nasC, SHHBd, nrbond, nelem, SsCH3, eaC2C2a, e1C3O1a, SHCsatu, Qv, nvx.
   c. Within a Java main executable program, create an instance of the ODTNeuralNetworksDescriptors class.
   d. Using the setter methods of the ODTNeuralNetworksDescriptors instance, set the values of all of the descriptors listed in step 2b.
   e. Within the same Java main executable program, create an instance of the ODTNeuralNetworks class, using the instance of the ODTNeuralNetworksDescriptors created in step 2d as a parameter argument.
   f. Within the same Java main executable program, retrieve the computed odor detection threshold value for the given perfume raw material by calling the getODTModelResult( )method on the ODTNeuralNetworks instance created in step 2e.

The perfume mixture may have one of the aforementioned OI ranges and have at least about 5%, by weight of the mixture, of PRMs having an ODT less than or equal to about 1 ppb, or about 10 wt. % of PRMs having an ODT less than or equal to about 1 ppb, or from about 10 wt. % to about 50 wt. % of PRMs having an ODT less than or equal to about 1 ppb, or at least about 20 wt. % of PRMs having an ODT less than or equal to about 1 ppb, or from about 20 wt. % to about 50 wt. % of PRMs having an ODT less than or equal to about 1 ppb, or at least about 30 wt. % of PRMs having an ODT less than or equal to about 1 ppb, or from about 30 wt. % to about 50 wt. % of PRMs having an ODT less than or equal to about 1 ppb, or at least about 10 wt. % of PRMs having an ODT from about 0.5 ppb to about 1 ppb, or from about 10 wt. % to about 50 wt. % of PRMs having an ODT from about 0.5 ppb to about 1 ppb.

Exemplary OI values of perfume mixtures suitable for the present invention are shown in Table 1.

TABLE 1

Calculated OI of Selected Perfume Mixtures

| | OI | Wt. % of PRMs with ODT ≤ 1.0 ppb | Average VP (ppb at 25° C.) | Molar Average ODT |
|---|---|---|---|---|
| Perfume Mixture 1 RA | 60713 | 18.60 | 236842 | 39.3 |
| Perfume Mixture 2 KR | 39813 | 8.42 | 150000 | 68.5 |
| Perfume Mixture 3 LF | 43993 | 13.07 | 117105 | 32.9 |
| Perfume Mixture 4 GS | 52270 | 17.81 | 128947 | 23.6 |
| Perfume Mixture 5 SJ | 26539 | 10.85 | 106579 | 41.7 |
| Perfume Mixture 6 AT | 95753 | 5.57 | 310000 | 26.7 |
| Perfume Mixture 7 FL | 47602 | 5.77 | 170000 | 40.2 |
| Perfume Mixture 8 SM | 12891 | 6.15 | 150000 | 36.2 |
| Perfume Mixture 9 PP | 41375 | 16.48 | 97368 | 25.6 |

The perfume mixture may comprise about 45 wt. % to about 85 wt. % of PRMs having a weighted average VP range from about 15,000 ppb to about 20,000 ppb; or about 50 wt. % to about 80 wt. % of PRMs having a weighted average VP range from about 15,000 ppb to about 20,000 ppb; or about 55 wt. % to about 75 wt. % of PRMs having a weighted average VP range from about 15,000 ppb to about 20,000 ppb. The VP range of an exemplary perfume mixture is shown in Table 2.

TABLE 2

| Wt. % | Average VP (ppb @ 25° C.) | Lo VP (ppb @ 25° C.) | Hi VP (ppb @ 25° C.) |
|---|---|---|---|
| 6.00-10.00 | 131579 | 148684 | >148684 |
| 8.00-12.00 | 98684 | 115132 | 82237 |
| 10.00-14.00 | 65789 | 82237 | 49342 |
| 15.00-19.00 | 32895 | 42763 | 23026 |
| 17.00-21.00 | 13158 | 14868 | 11513 |
| 15.00-19.00 | 9868 | 11513 | 8224 |
| 9.00-13.00 | 6579 | 8224 | 4934 |
| 3.00-7.00 | 3289 | <2303 | 2303 |

Any commercially available PRM may be used in a perfume mixture having the OI range suitable for the present invention. PRMs materials include those listed in Table 3.

TABLE 3

| CAS | PRM | Mol. % | VP (ppb@ 25° C.) | ODT ppb |
|---|---|---|---|---|
| 109-60-4 | PROPYL ACETATE | 0.04 | 47236842 | 575 |
| 470-82-6 | EUCALYPTOL | 0.19 | 2169737 | 19 |
| 68039-49-6 | TRIPLAL | 1.46 | 760526 | 0.6 |
| 13254-34-7 | DIMETOL | 0.30 | 434211 | 88 |
| 6413-10-1 | METHYL DIOXOLAN | 16.54 | 288158 | 56 |
| 78-70-6 | LINALOOL | 2.80 | 119079 | 22 |
| 140-11-4 | BENZYL ACETATE | 14.34 | 215789 | 145 |
| 112-31-2 | ALDEHYDE C-10 | 0.18 | 272368 | 1 |
| 60-12-8 | PHENYL ETHYL ALCOHOL | 5.31 | 97500 | 11 |
| 67634-00-8 | ALLYL AMYL GLYCOLATE | 0.08 | 52632 | 16 |
| 5413-60-5 | CYCLACET | 8.25 | 18026 | 12 |
| 25265-71-8 | DIPROPYLENE GLYCOL | 0.02 | 12947 | 58 |

TABLE 3-continued

| CAS | PRM | Mol. % | VP (ppb@ 25° C.) | ODT ppb |
|---|---|---|---|---|
| 627-93-0 | DIMETHYL ADIPATE | 4.55 | 95395 | 21 |
| 27538-09-6 | ETHYL FRAISON | 0.01 | 15921 | 24 |
| 24851-98-7 | HEDIONE | 1.27 | 934 | 1 |
| 101-86-0 | HEXYL CINNAMIC ALDEHYDE | 1.00 | 917 | 0.2 |
| 77-93-0 | TRIETHYL CITRATE | 0.03 | 230 | 61 |
| 32210-23-4 | VERTENEX | 29.28 | 135526 | 2 |
| 106-24-1 | GERANIOL | 0.93 | 17500 | 0.4 |
| 121-32-4 | ETHYL VANILLIN | 0.13 | 1163 | 0.05 |
| 18479-58-8 | DIHYDRO MYRCENOL | 9.22 | 218421 | 69 |
| 91-64-5 | COUMARIN | 0.20 | 1711 | 0.7 |
| 104-67-6 | UNDECALACTONE/GAMMA | 1.56 | 3566 | 0.4 |
| 104-61-0 | NONALACTONE/GAMMA | 0.92 | 11289 | 2 |
| 28940-11-6 | CALONE 1951 | 0.05 | 1093 | 363 |
| 97-53-0 | EUGENOL | 1.32 | 13684 | 3 |
| 141-13-9 | ADOXAL | 0.02 | 3382 | 10 |
| | Sum | 100 | | |

The perfume mixture may also contain non-volatile components, such as known carrier materials including water, solvents, etc. The perfume mixture may have less than 35%, or less than 25%, by weight the perfume mixture, of solvents that are known in the art.

Perfume mixtures of the present invention may be present in a composition having additional ingredients that are known in the art. For example, the perfume mixture may be combined with carriers, as previously discussed, and/or with malodor ingredients to neutralize odors. Suitable malodor perfume mixtures include cyclodextrin, polyamine polymers, reactive aldehydes and ionones. In such case, the perfume mixture of the present invention may be used in any amount, including 50% to 100%, by weight of the composition, of the perfume mixture and 30% to 50%, by weight of the composition, of one or more carriers; or 0.001% to 10%, by weight of the composition, of the perfume mixture and 90% to 99%, by weight of the composition, of the additional ingredients.

Where the perfume mixture of the present invention is used with a fluid transport member such as a commercially available wick or breathable membrane, the viscosity of the perfume mixture may be considered as it may control how and when the PRM is delivered to the fluid transport member. For example, less viscous PRMs may flow faster than the more viscous PRMs. The more viscous PRM, being slightly less or of similar density with the less viscous phase, may remain in a perfume mixture reservoir via gravity. Thus, the less viscous PRM may be delivered to the transport member and emitted to the atmosphere more quickly. The PRMs may have viscosities less than about 23 cP and surface tension less than about 33 mN/m. In one embodiment, the perfume mixture containing a PRM may have a viscosity of about 1.0 cP to less than about 25 cP, alternatively about 1.0 cP to less than about 23, alternatively about 1.0 cP to less than about 15 cP.

The perfume mixture may be designed such that the perfume mixture may include a surface tension of about 19 mN/m to less than about 33 mN/m, alternatively about 19 mN/m to less than about 30 mN/m, alternatively about 19 mN/m to less than about 27 mN/m.

Method

The present invention includes a method of diffusing the perfume mixture described herein into a space. The method may comprise the step of providing any air freshening device having an evaporation assistance element and a delivery engine. The evaporation assistance element may be a fan assembly. The delivery engine has a liquid volatile perfume mixture therein and a fluid transport member, such as a breathable membrane or wick, in fluid communication with the liquid perfume mixture. The method includes activating via a power source the evaporation assistance element. In some embodiments, where the evaporation assistance element includes chemistry or an agitator, the activation step may include adding effective amounts of the chemical evaporation assistance element or manual agitation of the device and/or delivery engine to assist with evaporating the liquid volatile perfume mixture. The method of the present invention also includes activating the evaporation assistance element according to a duty cycle as disclosed herein.

EXAMPLES

Perfume Intensity Test

Perfume mixtures 1 to 9 in Table 1 herein were tested for scent intensity against a Control Mixture, as shown in Table 4.

TABLE 4

| Calculated OI of Control Mixture | | | |
|---|---|---|---|
| OI | Wt. % having an ODT ≤ 1.0 ppb | Average VP (ppb at 25° C.) | Molar Average ODT (ppb) |
| 18917.62 | 16.31 | 77000 | 20.5 |

Sensory Room Description: large rooms are 15'×15'×8' tall. The rooms have three glass walls, with a glass door on the front-most wall. The back wall is an aluminum panel and the ceiling is likewise aluminum. The floor is industrial grade tile covering. This room construction eliminates perfume absorption into surfaces which is common with typical construction (drywall, linoleum tiles, etc.).

Perfume Intensity Evaluation Procedure

1. The sensory room air controller is set to purge, which removes air from the room to outside the building. This setting is maintained for a period of fifteen minutes.
2. A trained odor evaluator verifies that there is not any residual perfume or room odor present in the room. If residual odor remains in the room, step 1, above, is repeated.

3. Once the room is determined to have no residual odor, the sensory room air controller is then adjusted to two air exchanges per hour, and no auxiliary fan in the room. At this point the room is set to ramp to set points for testing. In this manner, the room temperature and humidity are adjusted to the desired set points for testing, which are room temperature of 70° F. and Humidity of no greater than 40%.
4. After the room has equilibrated to the desired setpoints, an evaluator enters the room and places the test product at the desired location within the room and activates (turns the device on) the device. The evaluator then leaves the room ensuring the door closes behind them (Doors are set to remain closed at all times unless physically opened to enter/exit the room). Trained odor evaluators enter the odor room and close the door.
5. The product remains undisturbed in the room for a period of 60 minutes. At the 1 hour timepoint, trained odor evaluators enter the room and perform perfume odor evaluations over the next sixty seconds, making observations on intensity, character and distribution within the room. All doors are closed upon entering/exiting the room and remain closed during the test period.

Perfume Intensity Scale:
81-100=very strong, i.e., extremely overpowering, permeates into nose, can almost taste it;
61-80=strong, i.e., very room filling, but slightly overpowering;
41-60=moderate, i.e., room filling, character clearly recognizable;
21-40=weak, i.e., can be smelled in all corners, still can recognize character;
1-20=very weak, i.e., cannot smell in all parts of the room;
0=no odor.

FIG. 1 shows that perfume mixtures according to the present invention provide surprising superior scent intensity even at Day 30.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" All percentages and ratios are calculated by weight unless otherwise indicated.

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A perfume mixture comprising an olfactive index ("OI") of at least about 12,000, wherein said perfume mixture comprises at least about 5 wt. % of perfume raw materials having an odor detection threshold ("ODT") less than or equal to about 1 ppb, and said perfume mixtures comprises about 45 wt. % to about 85 wt. % of perfume raw materials having a weighted average vapor pressure ("VP") range from about 15,000 ppb to about 20,000 ppb.

2. The mixture of claim 1, wherein said OI is at least about 25,000.

3. The mixture of claim 1, wherein said OI is from about 12,000 to about 100,000.

4. The mixture of claim 1, wherein at least about 10 wt. % of said perfume mixture comprises perfume raw materials having a ODT less than about 1 ppb.

5. The mixture of claim 1, wherein at least about 10 wt. % of said perfume mixture comprises perfume raw materials having a ODT from about 0.5 ppb to about 1 ppb.

6. The mixture of claim 1, wherein about 50 wt. % to about 80 wt. % of said perfume mixture comprises a weighted VP range from about 15000 ppb to about 20000 ppb at 25° C.

7. The mixture of claim 1, wherein about 55 wt. % to about 75 wt. % of said perfume mixture comprises a weighted VP range from about 15000 ppb to about 20000 ppb at 25° C.

8. The mixture of claim 1, wherein said perfume mixture comprises less than about 35 wt. % of a solvent.

9. The mixture of claim 1, wherein the perfume mixture further comprises less than about 20 wt. % of a solvent.

10. A method of formulating a perfume mixture for use with an energized air freshener comprising the steps of calculating the average OI of said perfume mixture, and selecting perfume raw materials that provide a perfume mixture with an average OI of at least about 12,000, wherein said perfume mixture comprises at least about 5 wt. % of perfume raw materials having an odor detection threshold ("ODT") less than or equal to about 1 ppb, and said perfume mixtures comprises about 45 wt. % to about 85 wt. % of perfume raw materials having a weighted average vapor pressure ("VP") range from about 15,000 ppb to about 20,000 ppb.

11. The method of claim 10, wherein said average OI is at least about 25,000.

12. The method of claim 10, wherein said average OI is from about 25,000 to about 100,000.

* * * * *